(12) United States Patent
Phan et al.

(10) Patent No.: US 7,173,648 B1
(45) Date of Patent: Feb. 6, 2007

(54) SYSTEM AND METHOD FOR VISUALLY MONITORING A SEMICONDUCTOR PROCESSING SYSTEM

(75) Inventors: Khoi Phan, San Jose, CA (US); Bharath Rangarajan, Santa Clara, CA (US); Bhanwar Singh, Morgan Hill, CA (US); Bryan Choo, Mountain View, CA (US)

(73) Assignee: Advanced Micro Devices, Inc., Sunnyvale, CA (US)

( * ) Notice: Subject to any disclaimer, the term of this patent is extended or adjusted under 35 U.S.C. 154(b) by 0 days.

(21) Appl. No.: 09/553,841

(22) Filed: Apr. 21, 2000

(51) Int. Cl.
*H04N 7/18* (2006.01)
*G01N 21/00* (2006.01)

(52) U.S. Cl. .................. 348/87; 356/237.1; 356/237.5

(58) Field of Classification Search .................. 348/87, 348/126, 131; 382/141, 144, 145; 430/30, 430/311, 325; 438/16, 949; 356/436, 442, 356/237.1, 237.3, 237.5; 396/569, 570; 250/573
See application file for complete search history.

(56) References Cited

U.S. PATENT DOCUMENTS

| | | | |
|---|---|---|---|
| 4,647,172 A * | 3/1987 | Batchelder et al. ......... 396/569 |
| 4,816,098 A | 3/1989 | Davis et al. | |
| 4,851,311 A * | 7/1989 | Millis et al. .................. 430/30 |
| 4,980,971 A | 1/1991 | Bartschat et al. | |
| 5,002,008 A | 3/1991 | Ushijima et al. | |
| 5,091,692 A * | 2/1992 | Ohno et al. ................. 324/758 |
| 5,455,894 A | 10/1995 | Conboy et al. | |
| 5,725,663 A | 3/1998 | Parrette | |
| 5,742,395 A * | 4/1998 | Biedermann et al. ....... 356/394 |
| 5,788,868 A | 8/1998 | Itaba et al. | |
| 5,843,527 A * | 12/1998 | Sanada ....................... 427/240 |
| 5,863,680 A | 1/1999 | Kawakubo et al. | |
| 5,927,077 A | 7/1999 | Hisai et al. | |
| 5,940,175 A * | 8/1999 | Sun ......................... 356/237.3 |
| 5,963,314 A * | 10/1999 | Worster et al. .......... 356/237.2 |
| 5,966,635 A | 10/1999 | Hiatt et al. | |
| 6,002,572 A | 12/1999 | Hirose et al. | |
| 6,089,763 A * | 7/2000 | Choi et al. ................. 396/611 |
| 6,603,874 B1 * | 8/2003 | Stern et al. ................. 382/144 |

* cited by examiner

*Primary Examiner*—Gims Philippe
*Assistant Examiner*—Erick Rekstad
(74) *Attorney, Agent, or Firm*—Amin, Turocy, & Calvin, LLP

(57) ABSTRACT

The present invention relates to visually monitoring an interior portion of a processing chamber in a semiconductor processing system. An image collector collects images of the interior of the chamber and provides an image signal indicative of a visual representation of the interior of the chamber. A viewing station receives the image signal and displays a visual representation of the interior of the chamber.

23 Claims, 4 Drawing Sheets

SYSTEM AND METHOD FOR VISUALLY MONITORING A SEMICONDUCTOR PROCESSING SYSTEM

TECHNICAL FIELD

The present invention relates generally to semiconductor processing and, more particularly, to a system and method for visually monitoring a semiconductor processing system.

BACKGROUND OF THE INVENTION

The tendency of semiconductor devices such as integrated circuits (IC) and large scale integrated circuits (LSIC) toward minuteness has rapidly progressed, and higher accuracy and efficiency have been required of apparatuses for manufacturing such semiconductor devices. Semiconductor integrated circuits undergo a variety of processing steps during manufacture, such as masking, resist coating, developing, etching, and deposition. In many of these steps, material is applied or removed from a substrate within an enclosed chamber having a controlled environment.

In order to remain competitive, manufacturers of semiconductor devices continually strive to improve production yields, while at the same time reducing the associated manufacturing costs. As their customers increasingly require larger quantities of semiconductor products, the manufacturers seek equipment capable of operating efficiently for producing products commensurate with the customers' expectations. Because floor space is at a premium in most manufacturing facilities (due to the clean room environment necessary for fabrication of semiconductor devices), the manufacturers of semiconductor processing equipment have responded by producing semiconductor processing systems having vertically integrated processing units.

One particular example of a vertically integrated system is a coater/developer track system, which is often being manufactured at heights of about ten feet or greater. In such a system, for example, multiple coater and/or developer units are vertically stacked on top of each other, typically at the upper part of the track system.

SUMMARY OF THE INVENTION

The present invention relates to a system and method for visually monitoring a semiconductor processing system.

An image collector is associated with an enclosed processing chamber of a semiconductor processing system. The image collector collects images of the interior of the chamber and provides an image signal to a viewing station indicative of visual representation of the chamber interior. A technician may visually inspect the chamber interior at a display associated with the viewing station based on image signal.

One aspect of the present invention relates to a system for visually monitoring a semiconductor processing system. The system includes an enclosed processing chamber having an interior. An image collector is associated with the chamber for collecting images of the interior of the chamber and providing an image signal indicative of a visual representation of the interior of the chamber.

Another aspect of the present invention relates to a system for visually monitoring a semiconductor processing system. The system includes imaging means for collecting images of an interior of an enclosed processing chamber of the semiconductor processing system and providing an image signal indicative of a visual representation of the interior of the chamber; and display means for processing the image signal and displaying a visual representation of the interior of the chamber.

Another aspect of the present invention relates to a method for monitoring an interior of an enclosed processing chamber in a semiconductor processing system. The method includes collecting images of the interior of the chamber and providing a signal indicative of a visual representation thereof.

To the accomplishment of the foregoing and related ends, the invention, then, comprises the features hereinafter fully described and particularly pointed out in the claims. The following description and the annexed drawings set forth in detail certain illustrative examples of the invention. These examples are indicative, however, of but a few of the various ways in which the principles of the invention may be employed. Other objects, advantages and novel features of the invention will become apparent from the following detailed description of the invention when considered in conjunction with the drawings.

DETAILED DESCRIPTION OF THE INVENTION

Figure 1:
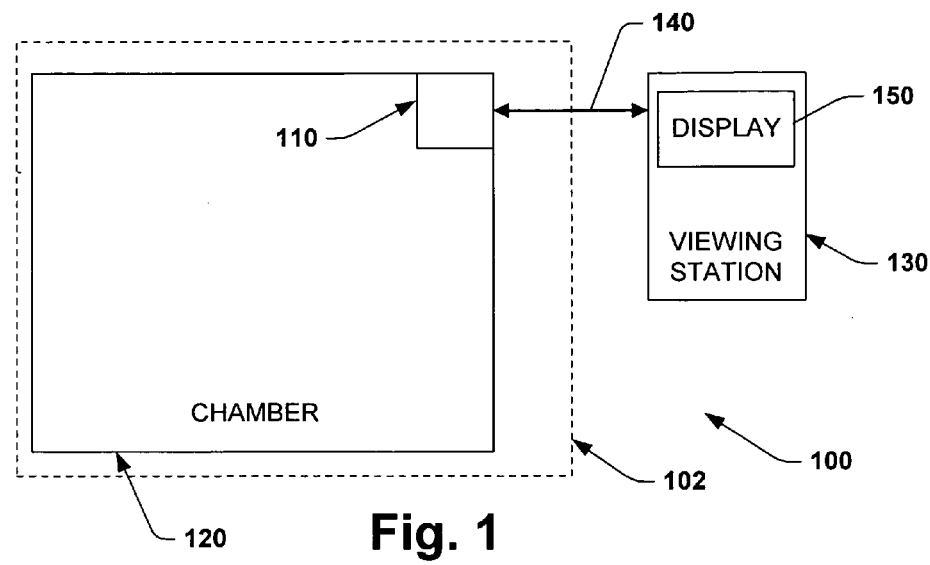
FIG. 1 is a schematic block diagram of an enclosed chamber of a semiconductor processing system equipped with an image collector in accordance with the present invention.

The present invention will now be described with reference to the drawings, wherein like reference numerals are used to refer to like elements throughout.

FIG. 1 is a schematic block diagram of a system 100 for monitoring a semiconductor processing system 102 in accordance with the present invention. The system 100 includes an image collector 110, such as a very small analog or digital camera, associated with an enclosed chamber 120 of the processing system 102. In particular, part of the image collector 110 is located within the interior of the chamber 120 for collecting images of the contents and operation within the chamber. The image collector 110 provides a signal indicative of a visual representation of the interior of the chamber 120 to a viewing station 130 via a communications link 140. The viewing station 130 includes a display 150 (e.g., a PC monitor or TV screen) at which a technician may visually inspect the interior of the chamber 120 according to the collected images.

The viewing station 130 is located at a convenient location so that a technician may readily view the associated display 150 for visually inspecting the interior contents of the chamber 120. The viewing station 130 may, for example, be located remote from the chamber 120, such as located at a console outside a clean room in which the processing system 102 is situated. Alternatively, the viewing station 130 could be integrally connected with the system 102 in which the chamber 120 is mounted. Depending mainly on the location of the system 102 relative to the viewing station, the communications link 140 between the image collector 110 and the viewing station may be wired or wireless. The term "wired" as used herein is intended to include any physical communications link, including, for example, an electrically conducting cable and a fiber optical link. Similarly, the term "wireless" is intended to cover any form of communication that utilizes air as a transmission medium, including, for example, electromagnetic, optical, and acoustic forms of communication links. The communication over the link 140 may be analog or digital. In addition, the communications link 140 may be bidirectional, in which operation of the image collector 110 is controlled by a controller associated with the viewing station 130. For example, the image collector 110 may be manually activated by a switch device at the viewing station 130. Alternatively, the image collector 110 could be activated automatically, such as in response to sensing equipment (not shown) associated with the chamber 120 indicating that conditions of the chamber 120 are not within expected operating parameters. In such situations, a warning alarm at the viewing station 130 also may be activated to assist the technician in troubleshooting efforts.

By way of example, the system 102 of FIG. 1 is a track system in which semiconductor wafers are loaded into, processed, and unloaded. In the track system, the chamber 120 is a processing unit, such as a coater, developer, heating unit, cooling unit, etc. The wafers are placed into the processing chamber 120 and subjected to various controlled processes, such as resist coating, developing, heating, and/or cooling. The image collector 110 and the viewing station 130 collectively provide a mechanism by which a technician may visually inspect the progress and/or troubleshoot the operations within the processing chamber 120.

Figure 2:
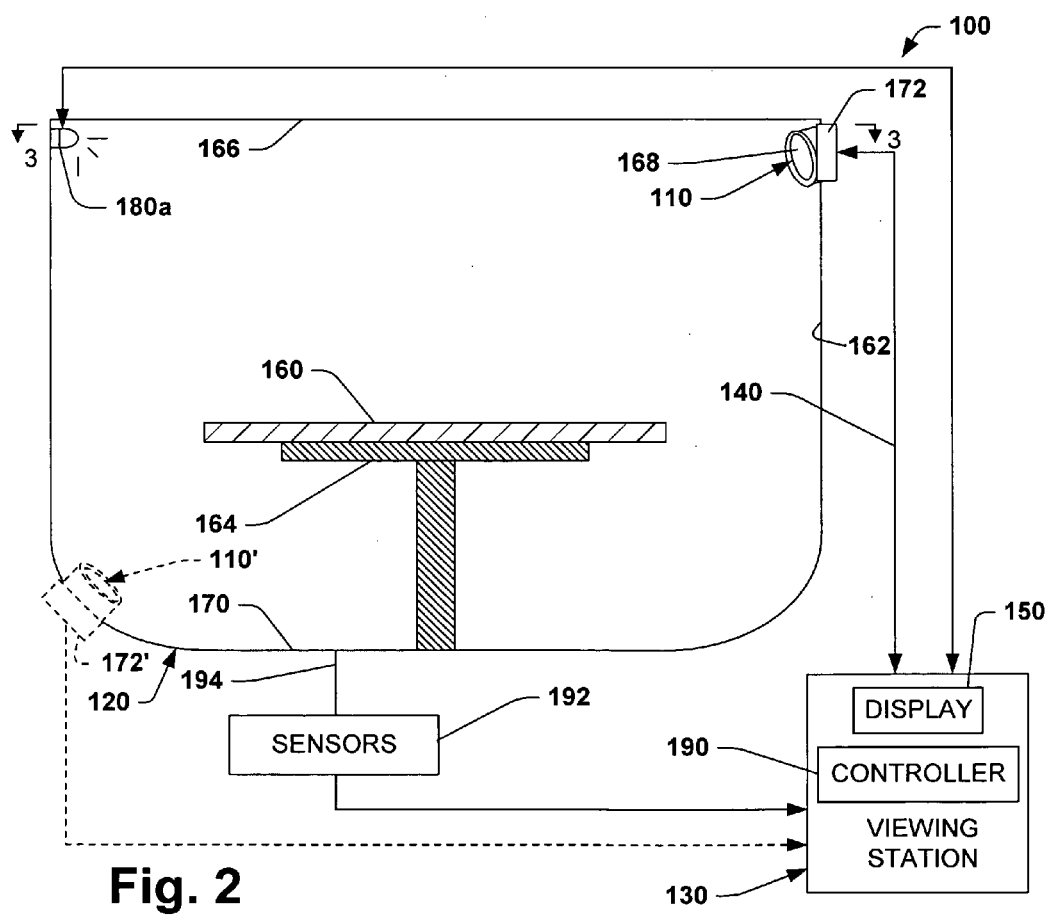
FIG. 2 is side sectional view of an enclosed processing chamber equipped with an image collector in accordance with the present invention.
Figure 3:
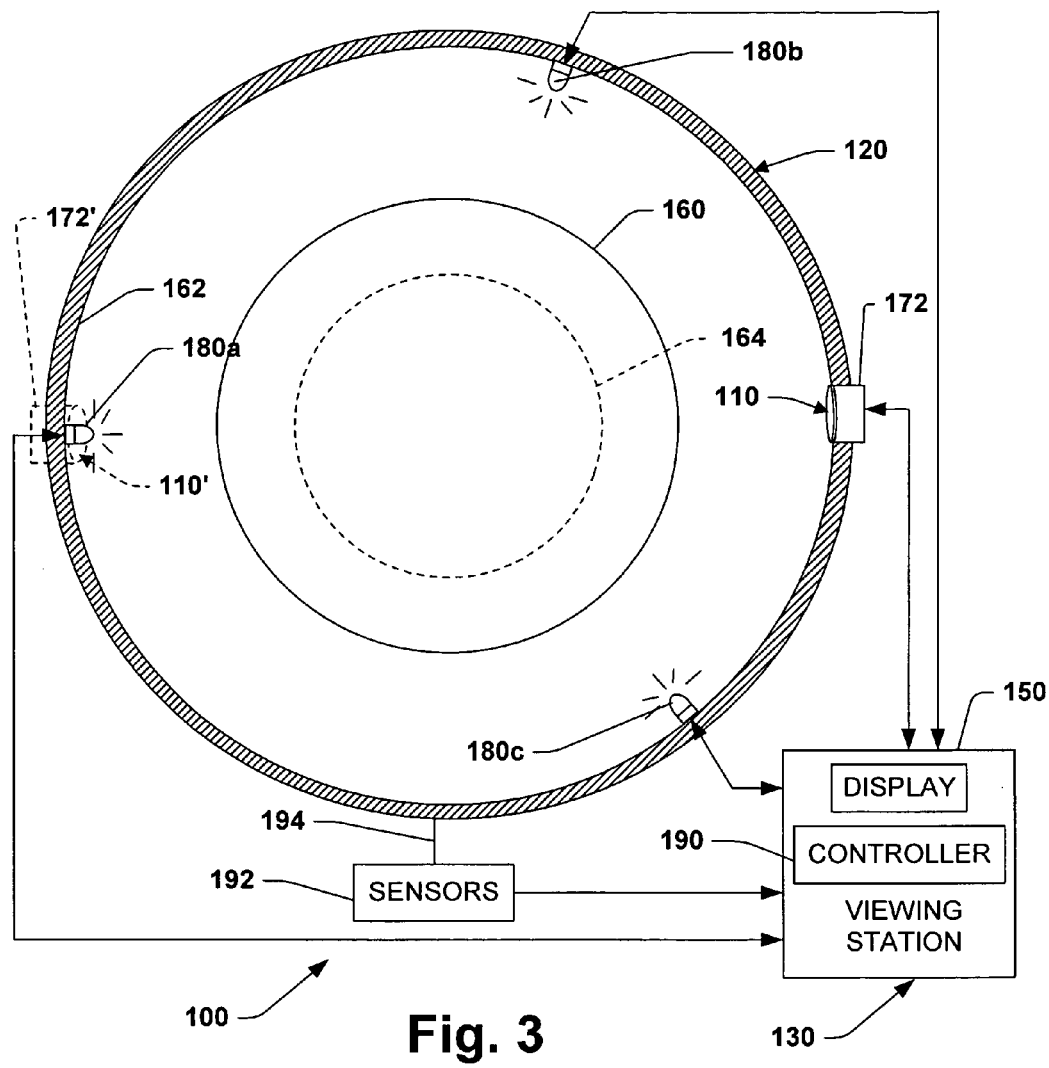
FIG. 3 is a sectional view taken along line 3—3 of the chamber of FIG. 2.

FIGS. 2 and 3 illustrate a schematic illustration of a system 100 for monitoring an interior chamber 120 of a semiconductor processing system in accordance with the present invention. The processing chamber 120 is configured for receiving and processing a wafer 160 in a predefined manner. In particular, the chamber 120 is a cup or container, such as part of a processing unit (e.g., a coater or developer) of a track system. The chamber 120 has a cylindrical sidewall 162 which encloses a rotatable chuck 164 onto which the wafer 160 (or other substrate) is mounted for processing. The chuck 164 typically includes a vacuum system (not shown) for holding the wafer 160 on its surface during processing.

In a spin processing unit, for example, a nozzle (not shown) typically supplies a predetermined amount of viscous material (e.g., resist or solvent) onto the wafer 160. The chuck 164 and wafer 160 are then accelerated to and rotated at a certain speed, and centrifugal forces exerted on the viscous material cause the material to disperse over the surface of the wafer. It will be appreciated that, for purposes of the present invention, the features of the monitoring system 100 are applicable to all types of enclosed wafer processing units.

In accordance with the present invention, an imaging collecting device 110 is operatively associated with the chamber 120 for collecting visual images of the interior of the chamber. In the example of FIGS. 2 and 3, the image collector 110 is a substantially miniature solid state camera, such as a CCD or digital video camera, although other types of cameras also could be used. The image collector 110 is mounted to the sidewall 162 near to a top end 166 of the chamber 120. The image collector 110 includes a lens 168 located within the chamber 120 and oriented at an angle so as to see the wafer 160 located on the chuck 164. Preferably, the lens 168 is a wide angle lens capable of viewing substantially the entire interior portion of the chamber 120 within the field of view of the lens.

It will be appreciated that while one image collector 110 mounted within the chamber 120 (as shown in FIG. 2) may be sufficient for monitoring purposes, more than one image collector may be employed for more detailed viewing of different selected interior portions of the chamber 120. For example, another camera (indicated in phantom at 110') optionally could be located at a bottom end 170 of the chamber so as to collect images of a lower portion of the chuck 164 and the mounting arrangement of the wafer 160 and chuck. Each image collector 110, 110' should be mounted in an unobtrusive manner (substantially flush with the sidewall) so as not to interfere with processing within the chamber 120. In the solid state camera example of FIGS. 2 and 3, electronics 172 and 172' associated with devices 110 and 110', respectively, are located outside the chamber 120 so as to minimize interference with operation of the chamber.

One or more sources of light 180$a$, 180$b$, and 180$c$ (collectively referred to as 180) also are operatively connected within the chamber 120 for illuminating the contents of the chamber to facilitate image collecting by the image collector 110. By way of example, the light sources 180 are light emitting diodes (LEDs) located at circumferentially spaced apart locations mounted to the sidewall 162 near the top end 166 of chamber 120. The LEDs usually are selected to provide light at a wavelength so as not expose photoresist material being employed (in a developer or coater unit). For example, yellow light may be used when the photoresist is responsive to ultraviolet light.

The monitoring system 100 also includes a controller 190 for controlling operation of the image collector 110 and the light sources 180. While the controller 190 is illustrated as being part of the viewing station 130, it is to be understood that the controller could be separate from the viewing station, such as integrated as part of the associated system 102 (FIG. 1) or implemented as a stand-alone controller. The controller 190 is programmed to control and operate the image collector 110, light sources 180, viewing station 130, and other various components within the system 102 in order to carry out the various functions described herein. The manner in which the controller 190 can be programmed to carry out the functions relating to the present invention will be readily apparent to those having ordinary skill in the art based on the description provided herein. As mentioned above, the image collector 110 and/or light sources 180 may be manually activated (e.g., by a technician at the viewing station) and/or may be automatically activated by the controller 190 based on operating conditions of the chamber 120.

In order to sense operating conditions of the chamber 120, sensors 192 are operatively connected with the chamber to sense various operating parameters thereof. The operative connection between the sensors 192 and the chamber 120 is schematically illustrated at 194. The sensors 192 may be integrated sensors of the associated processing system 102 (FIG. 1) which are used to sense operating conditions associated with the chamber 120. The sensors 192 may be configured to sense a variety of operating conditions, such as, for example, temperature, pressure, vibration, rotation speed of the chuck 164, or any other condition useful in controlling the operation of the processing unit associated with the chamber 120. The sensors 192 provide sensor signals to the controller 190 indicative of the sensed operating conditions.

The controller 190 controls operation of the image collector 110 and light sources 180 in response to the sensor signals. By way of example, the controller 190 may activate the image collector 110 and/or light sources 180 if a sensor signal indicates that a selected aspect of the process within chamber 120 is outside an expected operating parameter. The controller 190 also might activate an alarm or warning signal to alert the technician of a potential abnormal operating condition. In addition, the controller 190 could be programmed to activate the image collector 110 and/or light sources 180 at predetermined times to permit the technician to visually inspect the internal operations of the chamber 120 at routine intervals.

The controller 190 also may be programmed to receive feedback related to the operation of each light source 180 and/or image collector 110. For example, the controller 190 might, based on feedback from the light sources 180, adjust the intensity of each light source to maintain a desired intensity of light within the chamber 120. The controller 190 also could rapidly activate and deactivate the light sources 180 in a strobe-light manner to help monitor and diagnose moving parts within the chamber 120 (e.g., chuck 164, nozzle arm (not shown)). Similarly, the controller 190 may selectively activate and deactivate the image collector 110 to control the rate at which images are collected.

With particular references to light sources 180, it may be desirable to selectively activate and deactivate different sources of light depending on the type of chamber 120 and/or the sensed operating conditions thereof. In a coater processing chamber, for example, light source 180a may be configured to emit light at a wavelength that matches the wavelength needed to expose photoresist and light sources 180b and 180c may be configured to emit light that does not expose the photoresist material. The controller 190 may activate light sources 180b and 180c at any time to facilitate collecting images within the chamber 120. However, the controller 190 limits activation of light source 180a to situations when no resist-coated wafer is within the chamber 120, such as to perform a cleaning function. In particular, the light source 180a performs a cleaning function by exposing remaining photoresist material within the chamber 120. The exposed resist is then easily removed from the chamber 120. A single light source 180a also may be configured to selectively emit light at two different wavelengths, such that the single source light provides a dual purpose. Specifically, the controller 190 may activate the light source 180a at a first wavelength to expose remaining resist material in the chamber 120 (e.g., for cleaning purposes) and at a second wavelength to illuminate the contents of the chamber to facilitate image collection.

The foregoing examples illustrate but a few approaches as to how one of ordinary skill in the art could program the controller 190 to control the monitoring system 100 in accordance with the present invention. It is to be appreciated that many other control methodologies could be implemented in accordance with the present invention and that all such control methodologies are intended to fall within the scope of the appended claims.

Figure 4B:
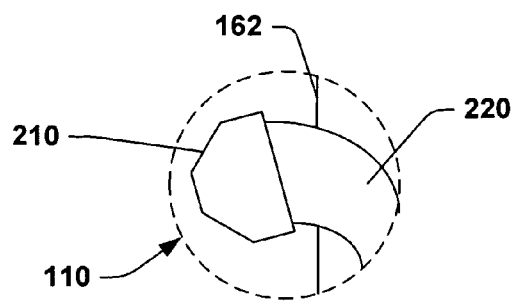
FIG. 4b is an enlarged view of part of the system of FIG. 4a, illustrating the image collector in greater detail.
Figure 4A:
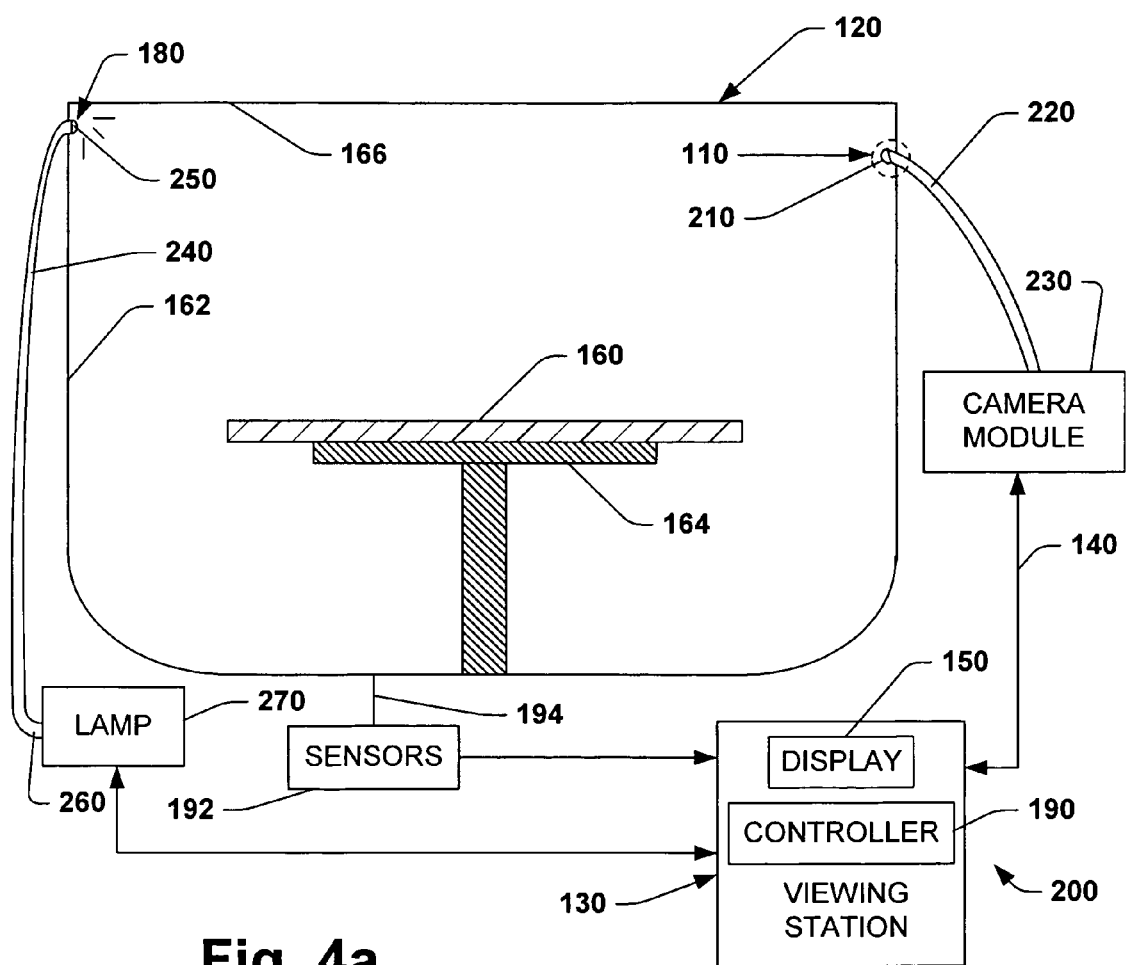
FIG. 4a is a side sectional view of an enclosed processing chamber equipped with an image collector in accordance with the present invention.

FIG. 4a is a schematic illustration of another system 200 for monitoring a semiconductor processing system in accordance with the present invention. Similar to the example of FIGS. 2 and 3, the monitoring system 200 includes an image collector 110 operatively associated with an enclosed processing chamber 120, such as a processing unit of a track system. The chamber 120 has a cylindrical sidewall 162 which encloses a chuck 164 onto which a wafer 160 is mounted for processing in accordance with the designed function of the chamber. The image collector 110 provides an image signal indicative of a visual representation of the interior of the chamber 120.

The image collector 110 is formed of a fiber optic camera including a lens portion 210 operatively connected to an end of a fiber optic cable 220. The lens 210 is mounted within the chamber 120 near its upper end 166 for collecting images of the interior of the chamber. The cable 220 may be an individual fiber cable or a bundle of cables. The fiber optic cable 220 extends from the lens 210 to a camera module 230 for providing an optical image signal according to the images received at the lens. In particular, the image signal is formed of light received at the lens 210 as reflected from the contents of the chamber 120. The camera module 230 includes, for example, a coupling lens and processing device for converting the optical image signal provided by the cable 220 into a corresponding electrical signal indicative of a visual representation of the interior of the chamber 120. The camera module 230 provides the electrical signal to a viewing station 130. The viewing station 130 processes the electrical signal to provide a visual representation of the interior of the chamber 120 at a display 150. The electrical signal also may be recorded at the viewing station 130 for subsequent viewing by a technician.

FIG. 4b illustrates an enlarged view of the lens 210 and fiber optic cable 220 that form the image collector 110. In this example, the lens 210 is faceted so as to receive light from a plurality of discrete directions within the chamber 120. The associated camera module 230 (FIG. 4a) converts the received optical image signal into an electrical signal which may include separable images corresponding to each faceted portion of the lens 210. Alternatively, the cable 220 may include a plurality of individual fiber cables, with each cable being associated with one or more facets of the lens 210. Another alternative is to provide each cable of the bundle with a separate lens. In each of the bundled cable approaches, each cable of the bundle provides an optical image signal indicative of an image for a corresponding portion of the interior of the chamber 120. Other lens configurations also could be used to collect images of the substantially the entire chamber interior.

Referring back to FIG. 4a, the system 200 includes a light source 180 for illuminating the contents of the chamber 120 to facilitate the image collection function of the fiber optic camera. The light source 180 in this example is formed of one or more fiber optic cables 240 having a portion 250 thereof disposed at a selected location within the chamber 120 for illuminating the interior contents of the chamber. Another end 260 of the fiber cable 240 is connected to a lamp module 270 which provides the light to cable. The lamp 270 may be integrated into the track system or it may be separate. While an end 250 of the cable 240 is illustrated as located in the chamber 120 for providing illumination, it is to be appreciated that a greater length of the cable 240 (e.g., mounted along an upper periphery of the interior of the chamber). Additional lighting accessories operatively associated with the cable 220 also could be disposed in the chamber 120 to provide desired illumination. As in the example of FIGS. 2 and 3, the lamp 270 is configured to provide light through the fiber optic cable at a selected wavelength so as not to expose photoresist material which may be present in the chamber 120 (unless such exposure is desired as described herein).

The monitoring system 200 includes a controller 190 programmed for controlling operation of the image collector 110, light source 180, viewing station 130, lamp 270, and other various components within the monitoring system 100 in order to carry out the various functions described herein. Sensors 192 are operatively connected with the chamber 120 to sense various operating parameters of the chamber and its operation. The sensors 192 provide a sensor signal to the controller 190 indicative of the sensed operating conditions. The controller 190 may be programmed to operate in a substantially identical manner to that described above.

Briefly stated, the controller 190 may be programmed to control operation of the image collector 110 and light source(s) 180 in response to the sensor signal and/or in response to feedback provided by the camera module 230 or lamp 270. For example, the controller 190 may activate the image collector 110 and/or light sources 180 if the sensor signal indicates that a selected aspect of the process within the chamber 120 is outside expected operating parameters. The controller 190 also might control the image collector 110 in response to the sensor signal to collect images at particular location in the chamber 120, such as by aiming the lens or adjusting its magnification level (e.g., by activating associated actuators (not shown)). In addition, the controller 190 could activate an alarm or warning signal (such as associated with the viewing station 130) to alert the technician of the potential abnormal operating condition.

It is to be understood that a plurality of cables and lenses may be used to visually monitor different selected portions within the chamber. For example, additional light sources and/or cameras may be located at the lower portion of the chamber 120 so as to monitor the mounting arrangement between the wafer 160 and chuck 164 (see FIGS. 2 and 3). In addition to monitoring the chuck 164 and wafer 160, the camera may be angled so as to view a nozzle arm (not shown) which may be located within the chamber 120. The nozzle arm, for example is used to apply photoresist (in a coater unit) or to apply a suitable solvent for removing exposed photoresist (in a developer unit).

Figure 5:
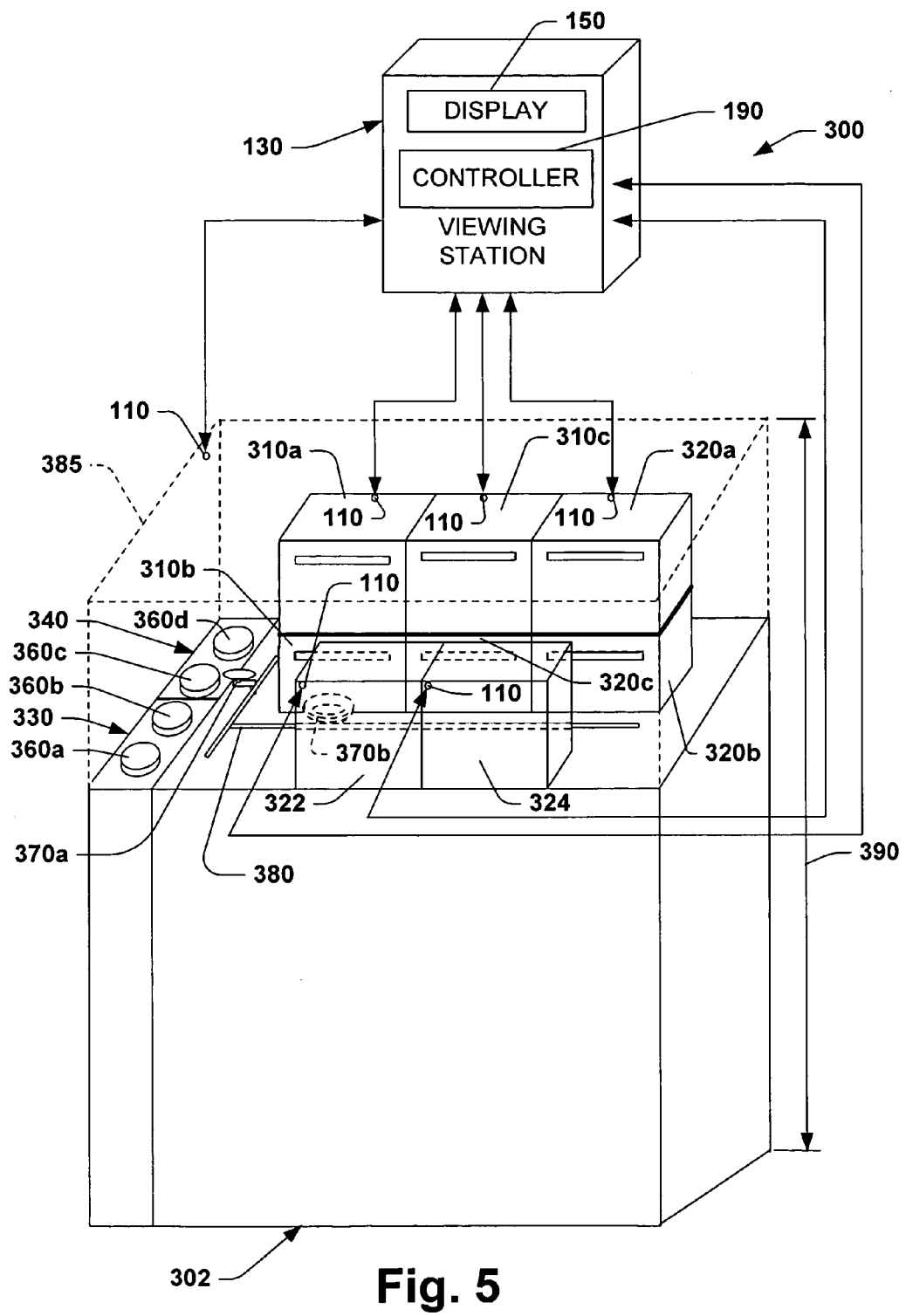
FIG. 5 is an isometric view of a schematic illustration of a track system equipped with image collectors in accordance with the present invention.

FIG. 5 is a representative schematic illustration of a system 300 for monitoring a plurality of processing units of an exemplary semiconductor processing track system 302 in accordance with the present invention. The track system 302 includes a plurality of vertically stacked spin coater units 310a, 310b, 310c (collectively referred to as 310) and spin developer units 320a, 320b, 320c (collectively referred to as 320). Other processing units 322 and 324 may be provided for implementing other required processing steps within the track system 302. For example, unit 322 may be a baking unit (heater) and unit 324 may be a cooling unit (cooler) for selectively exposing a wafer to different controlled temperatures during the wafer fabrication process.

The track system 302 includes receiving and sending sections 330 and 340, respectively, for storing cassettes 360a, 360b, 360c, 360d of wafers at different stages of the fabrication process. The track system 302 also includes several robotically actuated transport arms 370a, 370b (collectively referred to as 370). Each arm 370a, 370b includes a tray having an upper surface for receiving a wafer. The arms 370 move along tracks 380 or paths for transporting wafers between the storage cassettes 360 and the processing units 310, 320, 322, 324 of the system 302. Each of the processing units 310, 320, 322, 324 include doors through which the wafers are transported. While two arms 370 are illustrated in FIG. 5, it will be appreciated that several more could be placed on the tracks 380 for moving wafers through the various parts of the coating and developing processes. Additional tracks also could be provided to facilitate wafer transport.

For example, the receiving section 330 includes one cassette 360a which contains bare wafers to which a photoresist material is to be applied or coated in the coater units 310. The arms 370 transfer a wafer from the cassette 360a to a coater unit 310 which, for example, coats a selected photoresist material onto the wafer surface. Another of the cassettes 360b stores resist-coated wafers that have been selectively exposed to radiation, such as during a photolithography process. The arms 370 transport a wafer from the cassette 360b to a selected developer unit 320 which develops and/or removes the exposed photoresist, such as by application of a solvent. The sending section 340 includes cassettes 360c and 360d which store wafers after having been processed in the processing units 310 and 320. By way of example, cassette 360c receives and stores resist-coated wafers from the coater units 310 and cassette 360d receives and stores wafers after being processed in a developer unit 320.

As is representative of existing track systems, the processing units 310, 320, 322, and 324 are located at the top part of the track system 302, which is enclosed by a housing 385 (illustrated in phantom for ease of illustration). The track system 302 has a height, indicated at 390, which may be in excess of ten feet. While, under normal operating conditions, the track system 302 enables a manufacturer to increase production yields, the increased height has resulted in practical difficulties for semiconductor manufacturers. In particular, a technician has an average height ranging between about five and six feet. As a result, it is difficult for the technician to visually inspect vertically elevated parts of the system 302. In fact, the technician may be required to use a step ladder to visually inspect the contents of the system 302 components near the top of the system. The use of a ladder poses difficulties to access, which could result in injury should the technician fall from the ladder.

As mentioned above, the processing units 310, 320, 322, and 324 include enclosed processing chambers 120 (FIGS. 1–4a) which provide controlled environments for wafer processing. The controlled environment also mitigates contamination caused by, for example, particulate material and/or unwanted light. Consequently, additional difficulties arise if a technician wishes to monitor the interior of the enclosed processing units 310, 320, 322, and 324 or within the enclosure 385. For example, in order to visually inspect interior parts of the system 302, such as when troubleshooting a potential abnormal operating condition, it may be necessary to temporarily cease processing and/or remove various panels and components of the track system 302. This may result in unwanted down time, which may lead to a corresponding increase in manufacturing costs.

In accordance with the present invention, one or more image collectors 110 are integrated into each processing unit 310, 320, 322, 324. Additional image collectors 110 also are located within the housing 385 of the track system 302 to collect images of, for example, the transport arms 370, cassettes 360, and tracks 380. The image collectors 110, which may be solid state or fiber optic instruments (e.g., cameras), are mounted in the enclosed chamber provided by each processing unit 310, 320, 322, 324 and the housing 385 to collect images of internal system parts and operation not easily visible to the technician. The image collectors 110 provide corresponding image signals to a viewing station 130 for viewing at an associated display 150.

As shown and described with respect to FIGS. 2–4a, an appropriate light source 180 also may be provided within each of the processing units 310, 320, 322, 324 and housing 385 to facilitate the image collection by each respective image collector 110. The light source 180 includes one or more sources of light, such as a LED or fiber optic cable, for illuminating the interior contents of the track system 302 and the interior contents of the elevated processing units 310, 320, 322, 324. Each light source, like the cameras, is mounted within the chamber 120 (FIGS. 1–4a) so as to provide a minimal level of interference with the processing function of the chamber.

A controller 190 is programmed to control operation of the light sources 180 and image collectors 110, such as based on feedback provided by each respective image collector 110 and light source 180. In addition, sensors 192 (not shown in FIG. 5 for ease of illustration) may provide sensor signals to the controller 190 indicative of various sensed operating parameters of the track system 302. The sensors could be integrated sensors of the track system 302 and/or additional sensors provided to specifically facilitate the visual monitoring process in accordance with the present invention. The particular manner in which the controller 330 can be programmed will be readily apparent to those having ordinary skill in the art based on the description provided herein.

It will be appreciated that the track system 302 of FIG. 5 could be integrated with a stepper system into an integrated processing system. Additional coater and/or developer units also could be incorporated into the track system 302 to further increase the throughput. Each of the units may be equipped with an image collector and light source in accordance with the present invention.

What has been described above are examples of the present invention. It is, of course, not possible to describe every conceivable combination of components or methodologies for purposes of describing the present invention, but one of ordinary skill in the art will recognize that many further combinations and permutations of the present invention are possible. Accordingly, the present invention is intended to embrace all such alterations, modifications and variations that fall within the spirit and scope of the appended claims.

What is claimed is:

1. A system that visually monitors semiconductor processing, comprising:
    a develop chamber;
    an image collector located at least partially within the develop chamber, the image collector collects energy reflected from inside the develop chamber and transmits a signal indicative of interior of the chamber; and
    a controller that receives at least one sensor signal and selectively controls operation of the image collector in response to the received at least one sensor signal.

2. The system of claim 1 further includes a light source that illuminates the interior of the develop chamber to enable the image collector to obtain a visible image of the interior of the chamber.

3. The system of claim 2, the light source is a light emitting diode.

4. The system of claim 2, the light source is a fiber optic cable with a light emitting portion located within the develop chamber.

5. The system of claim 2, further comprises a coater chamber that provides photoresist material on a substrate, the light source provides light at a wavelength so as not to expose the photoresist material.

6. The system of claim 2, the develop chamber develops photoresist material on a substrate, the light source provides light at a wavelength so as not to expose the photoresist material.

7. The system of claim 2, the image collector includes a camera module that collects the images and provides an electrical signal indicative of a visual representation of the interior of the chamber.

8. The system of claim 7, the camera module is connected with one end of a fiber optic cable, a lens being connected with another end of the fiber optic cable for collecting the images from the interior of the chamber and providing the image signal to the camera module, the camera module converting the image signal into the electrical signal.

9. The system of claim 8, the lens is faceted to receive reflected light from a plurality of discrete directions within the chamber so that the image signal is formed of an image from each of the discrete directions.

10. The system of claim 7 further includes a viewing station that receives the electrical signal and displays a visual representation of the interior of the chamber according to the electrical signal.

11. The system of claim 10, the viewing station includes a controller that selectively controls activation of the camera module.

12. The system of claim 11, the controller further controls the light source.

13. The system of claim 1, the image collector includes a fiber optic cable having a light receiving end disposed within the chamber for collecting images of the interior of the chamber, another end of the fiber optic cable being connected to a camera module that provides the image signal indicative of the interior of the chamber, the camera module converting the image signal into an electrical signal indicative of the interior of the chamber.

14. The system of claim 13, the light receiving end of the fiber optic camera includes a lens for receiving light from a plurality of discrete directions within the chamber so that the image signal is formed of an image from each of the discrete directions.

15. A system that visually monitors an internal part of a semiconductor processing system, comprising:
    imaging means for collecting images of an interior of an enclosed developer and providing an image signal indicative of a visual representation of the interior of the developer;
    controller means for selectively controlling operation of the imaging means based on a received sensor signal; and
    viewing means for receiving the image signal and providing a visual representation of the interior of the chamber.

16. The system of claim 15, the imaging means includes a camera having a lens portion located within the chamber to collect the images and provide the image signal.

17. The system of claim 15 further includes illumination means for illuminating the interior of the chamber to facilitate collecting images of the interior of the chamber by the camera.

18. The system of claim 17 further includes means for selectively controlling at least one of the camera and the illumination means.

19. A method for visually monitoring an interior of an enclosed developing chamber in a semiconductor processing system, comprising:
    controlling an operation based upon at least one signal indicative of an operating condition;

collecting visual images of the interior of the chamber and providing an image signal indicative thereof; and displaying a visual representation of the interior of the enclosed chamber based on the image signal.

20. The method of claim 19 further comprising illuminating the interior of the enclosed chamber to facilitate collecting of visual images.

21. The method of claim 20, illuminating includes emitting light within the chamber at a wavelength which does not interfere with processing within the chamber.

22. The method of claim 19 further comprising controlling the steps of emitting and collecting so that the visual representation includes images of processing within the chamber.

23. The method of claim 19, visual representation is displayed remotely from the semiconductor processing system.

* * * * *